United States Patent [19]

James et al.

[11] Patent Number: 5,286,652
[45] Date of Patent: Feb. 15, 1994

[54] AUTOMATED SAMPLE INPUT MODULE

[75] Inventors: Michael S. James, New Castle; Robert C. Kirkpatrick, Bear, both of Del.; Frank J. DeMonte, West Chester, Pa.

[73] Assignee: Hewlett-Packard Company, Palo Alto, Calif.

[21] Appl. No.: 876,934

[22] Filed: May 1, 1992

[51] Int. Cl.$^5$ .................................. G01N 30/24
[52] U.S. Cl. ............................. 436/48; 422/63; 422/64; 422/70; 436/47; 436/43; 436/174; 436/180; 73/864.23; 73/864.21
[58] Field of Search .............. 422/63, 64, 65, 81, 422/100, 104, 70; 436/43, 47, 48, 54, 174, 180; 73/864.21, 864.23, 864.31

[56] References Cited

U.S. PATENT DOCUMENTS

| | | | |
|---|---|---|---|
| 4,478,095 | 10/1984 | Bradley et al. | 422/64 |
| 4,595,562 | 6/1986 | Liston et al. | 422/65 |
| 4,708,886 | 11/1987 | Nelson | 422/72 |
| 4,713,974 | 12/1987 | Stone | 73/864.23 |
| 4,861,553 | 8/1989 | Mawhirt et al. | 422/65 |
| 4,951,512 | 8/1990 | Mazza et al. | 422/64 |
| 5,008,081 | 4/1991 | Blau et al. | 422/64 |
| 5,151,184 | 9/1992 | Ferkany | 210/514 |

Primary Examiner—James C. Housel
Assistant Examiner—Long V. Le
Attorney, Agent, or Firm—Richard F. Schuette

[57] ABSTRACT

Methods for handling a plurality of sample containers to be processed by an instrument are disclosed. In a preferred embodiment, a retaining device holds the sample containers and is indexed to align one of the sample containers to a position where communication with a sample input port of the instrument is established. A stripper moves a sample container into engagement with the sample port and, most preferably, also urges the sample container into sealing engagement with the sample port. An interference fit created between the stripper an the sample container provides a positive force that permits the sample container to be withdrawn and returned to its initial position. A lower arm assembly is disclosed which acts as a stop relative to the sample container and thus, as the stripper continues to move while the sample container is being withdrawn it overcomes the force of the interference fit and disengages the stripper. The present invention permits a single sample container to be inserted into a thermal zone to reduce the effects of the thermal zone upon samples not being processed. The present invention is also useful for manipulating a plurality of columns such as capillary columns or columns packed with a sorbent.

4 Claims, 4 Drawing Sheets

AUTOMATED SAMPLE INPUT MODULE

CROSS-REFERENCE TO RELATED APPLICATIONS

This application is related to U.S. patent application Ser. No. 825,450 filed Jan. 22, 1992, now U.S. Pat. No. 5,193,703, incorporated herein by reference, which is a continuation of U.S. patent application Ser. No. 487,655, now abandoned.

FIELD OF THE INVENTION

The present invention relates to methods and apparatus for introducing samples into an instrument for processing. More specifically, the present invention relates to the automated handling of a queue of sample containers and their automatic, sequential insertion into an analytical instrument.

BACKGROUND OF THE INVENTION

Currently available instruments used in analytical chemistry such as supercritical fluid extraction instruments automatically may generate multiple fractions from a single sample input and, with the incorporation of automation such as a robotic manipulator, a plurality of samples can be processed in a relatively automated fashion. However, there are several drawbacks to such a solution. First, the capital costs of the an lytical instrument and the robotic manipulator together are frequently so high as to negate any productivity gained by automation. Secondly, many instruments are not "robot-friendly" and the programming and customized hardware required to automate such systems can make them impractical. Finally, even in those systems where the samples can be input via a robotic manipulator, if the analysis performed is relatively simple, the speed at which the samples must be changed will exceed the speed at which the robotic manipulator can perform its tasks, reducing the productivity benefits to less than a maximum value.

It would therefore be desirable to automate sample input to an analytical instrument in a relatively inexpensive manner. Accordingly, it is an object of the present invention to provide a simple, reliable, accurate and robust system for automated sample input that can be integrated into an analytical instrument.

Additionally, many processes are performed upon samples at elevated temperatures, while others require cooling the sample. In the past, if multiple samples were formed in a queue, many or all of the samples were placed within a thermal zone to bring them to the appropriate temperature. For example, an entire tray of samples might be placed in an oven. Such procedures, however, are thought to have deleterious effects upon the samples or at least some of the constituents of interest in the samples, thereby diminishing the accuracy of any quantitative analysis performed. In other words, the thermal "cross-talk" between the samples results in a situation whereby different samples have different sample histories. Thus, in the case of biological samples, constituents such as metabolites in the last sample from a tray that has resided in an oven while other samples were analyzed might have been adversely affected as compared to the first sample taken from the tray at a time that may have been hours earlier. It is therefore another object of the present invention to provide methods and apparatus for handling a plurality of samples and moving a sample into and out of a thermal zone in a manner such that only one sample at a time is exposed to the thermal zone, thereby creating substantially the same sample history for each sample. Another (secondary) object of the present invention is to provide for a plurality of customized flow paths in an instrument that makes use of automatic zero (minimal) dead volume coupling, automatic thermal zone coupling, and selectable insertion.

As used herein, the term "instrument" refers to a wide variety of devices, including, but not limited to analytical instruments. Although sample preparation instruments such as supercritical fluid extraction instruments represent a preferred application of the present invention, the methods and apparatus disclosed herein are useful in other instruments such as supercritical fluid chromatographs, liquid chromatographs, and gas chromatographs, as well as other types of instruments, such as spectrometers or supercritical fluid extraction (SPE) instrumentation. Generally, the term "instrument" is meant to apply to both instruments that perform analysis and instruments that perform sample preparation steps prior to analysis, as well as instruments that process a sample for other reasons, such creating a refined material or extracting a material for other uses.

SUMMARY OF THE INVENTION

These and other objects of the present invention are achieved by novel methods of handling a plurality of sample containers to be placed into communication with an instrument comprising sample input port, wherein the plurality of sample containers is disposed in a retaining means. In accordance with the present invention, the retaining means is indexed to substantially align one of the sample containers with the sample input port. Next, one of the sample containers moves into communication with the input port and a process is performed upon a sample contained in the sample container, after which the sample container is withdrawn from communication with the input port. Preferably, the sample container is displaced from the retaining means, and in a most preferred embodiment, a stripper causes this displacement by releasably engaging the sample container. The stripper then urges the sample container into communication with the input port to create an interference fit connection between the sample container and the stripper assembly. The force generated by this interference fit is also used to withdraw the sample from communication with the input port by moving the stripper. In certain preferred embodiments, the stripper must be disengaged from the sample container.

In certain embodiments, the methods of the present invention will also include the step of placing the sample container and the sample contained therein within a thermal zone. Preferably, this step results in the thermal zone only affecting one of the plurality of sample containers. A method for initializing the position of the retaining means relative to the sample input port is also disclosed that most preferably uses a relative encoder to determine the position of the retaining means.

The present invention also discloses novel apparatus for handling a plurality of sample containers containing samples to be processed by an instrument. The apparatus disclosed uses a retaining means that holds the plurality of sample containers, and a means for indexing the retaining means to align one of the sample containers with the input port of the instrument. A means for moving one of the sample containers into communication with the input port and a means for withdrawing the sample from communication with the input port are also provided. In some embodiments, a thermal zone is disposed between the sample input port and the retaining means, whereby one of the sample containers is placed within the thermal zone at a time by the means for moving one of the sample containers. This results in only one sample being affected by the thermal zone at one time.

In preferred embodiments, the retaining means comprises a rack for retaining the plurality of sample containers in fixed positions relative to one another, and most preferably is a circular plate in which the fixed positions are arrayed in a substantially circular pattern about a central axis. Most preferably, the means for indexing the retaining means comprises a stepper motor controlled by a computer, and an encoder for determining the position of the retaining means relative to the sample input port is also provided.

The means for moving one of the sample containers preferably comprises a stripper for engaging a portion of the sample container. The stripper is preferably connected to a carriage, whereby the sample container is at least partially displaced from the retaining means by the motion of the stripper. The carriage most preferably is moved along an axis using a power screw. The disclosed stripper preferably comprises means for urging the sample container into communication with the input port, whereby a interference fit connection is established between the stripper and the sample container. This interference fit permits the stripper to also act as the means for withdrawing the sample from communication with the input port. Due to this interference fit, however, these embodiments of the present invention must also be provided with a means for separating the stripper and the sample container. Preferably, this separation is accomplished by engaging the sample container, whereby the motion of the stripper and sample container relative to the retaining means breaks the interference fit connection. In a most preferred embodiment, bottom arms slidably connected to the retaining means are provided to engage the sample container.

DETAILED DESCRIPTION OF THE PREFERRED EMBODIMENTS

Figure 1:
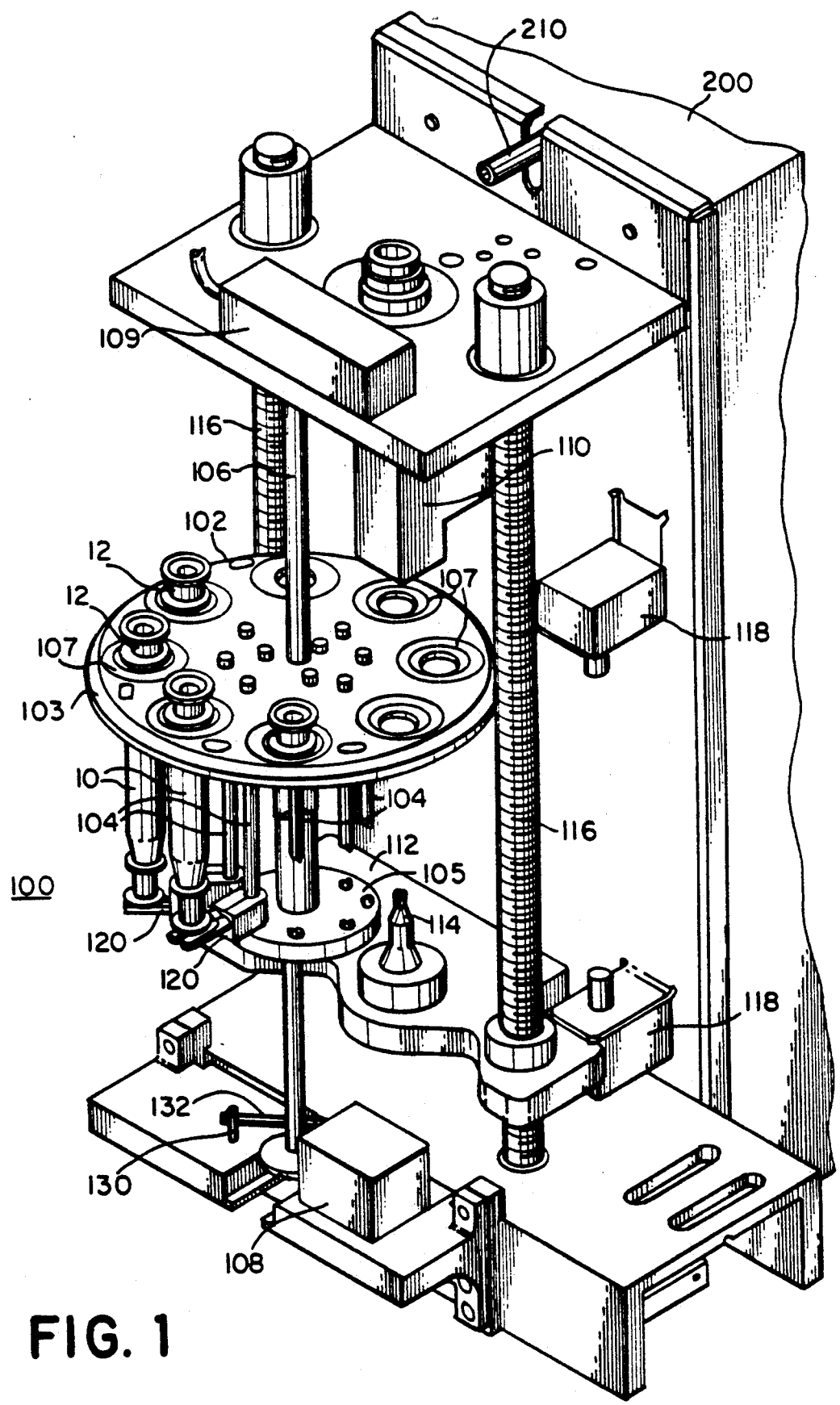
FIG. 1 is an perspective view of a preferred embodiment of the sample handling apparatus of the present invention.

Referring now to FIG. 1, there is shown a perspective view of a preferred embodiment of the apparatus 100 of the present invention. The apparatus 100 shown is preferably used in conjunction with an instrument 200 and most preferably provides a means for samples to be introduced into the sample input port 210 that forms part of the instrument 200. As will be readily understood by those of ordinary skill, the sample input port 210 may take many forms depending upon the nature of the sample, the nature of the analysis or processing to be performed and the pressure, flow rate and other parameters associated with the overall system. It will be further understood that FIG. 1 illustrates those portions of a typical system in which the present invention is useful and that, for clarity, wiring, pneumatic lines, brackets, safety shields, housings and other ancillary components of such systems have been omitted.

As seen in FIG. 1, a sample container 10 is disposed in a fixed location within a retaining means 102 such as a rack, preferably comprised of a circular plate 103 connected to a lower plate 105 by a center section 109. Several connecting rods 104 are disposed between the two plates. A sample retaining collar 107 preferably provides a stable fit between the sample container 10 and the top plate. For purposes of illustration, the sample retaining collar 107 and the sample containers 10 themselves are omitted from several of the locations in the top plate 103 illustrated in FIG. 1. It should be understood, however, that in operation, each location would most preferably contain one of a plurality of sample containers 10. As illustrated, the retaining means 102 is most preferably constructed to hold eight sample containers 10. Although this number can be varied, eight sample containers 10 represents an efficient sized queue for processes such as supercritical fluid extraction, wherein each extraction can require a time on the order of about one hour.

The sample container 10 is preferably closed using end caps 12 at either end, and in a most preferred embodiment, the end caps 12 are made in accordance with the invention disclosed in U.S. patent application Ser. No. 825,450 filed Jan. 22, 1992, which is incorporated herein by reference. As disclosed therein, end caps 12 for sealing a high pressure vessel may be constructed whereby a nominal seal is created upon engagement of the end cap 12 with threads on the inside of the vessel being sealed. Upon the application of a compressive force to the sample container, a sliding portion of the end cap 12 is urged against the vessel and forms a high pressure seal. A feature of such end caps 12 that makes their use desirable in conjunction with the present invention is that a zero dead volume connection may be established with the input port 210 of the instrument 200, which minimizes the flow disruption through the sample container.

A center axis 106 is fixed to the circular plate 103 and the lower plate 105 such that any rotation of the center axis 106 causes the retaining means 102 to rotate. The rotation of the retaining means 102 permits each one of the plurality of sample containers 10 to be substantially aligned with the sample input port 210 described above. As explained in further detail below, this indexed motion also aligns the sample containers 10 with a thermal zone 110 provided in preferred embodiments of the present invention to heat or cool the sample container and thus the sample contained therein to a predetermined temperature as required by the process being performed. Most preferably, the center axis 106 is rotated using a stepper motor 108 that can precisely index the rotation of the retaining means 102. The position of the retaining means 102, and thus information pertaining to the sample container 10 that is aligned with the sample input port 210, is determined using an encoder 109. As explained more fully below, the present invention preferably uses a relative encoder 109 which, after proper initialization, functions in a manner similar to an absolute encoder since the center axis 106 has a maximum rotational travel of less than a full revolution.

Figure 2A:
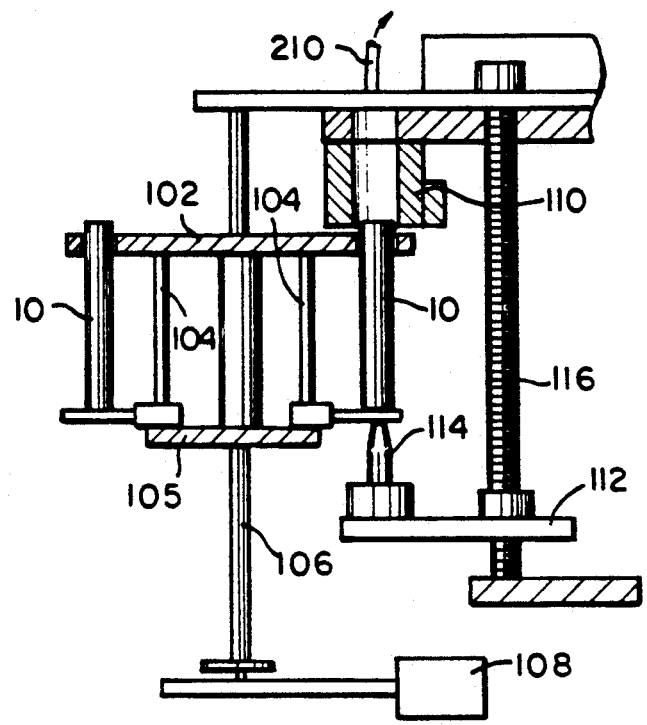
FIGS. 2A-2B are diagrammatic representations of the handling of a sample container in accordance with the present invention.
Figure 2B:
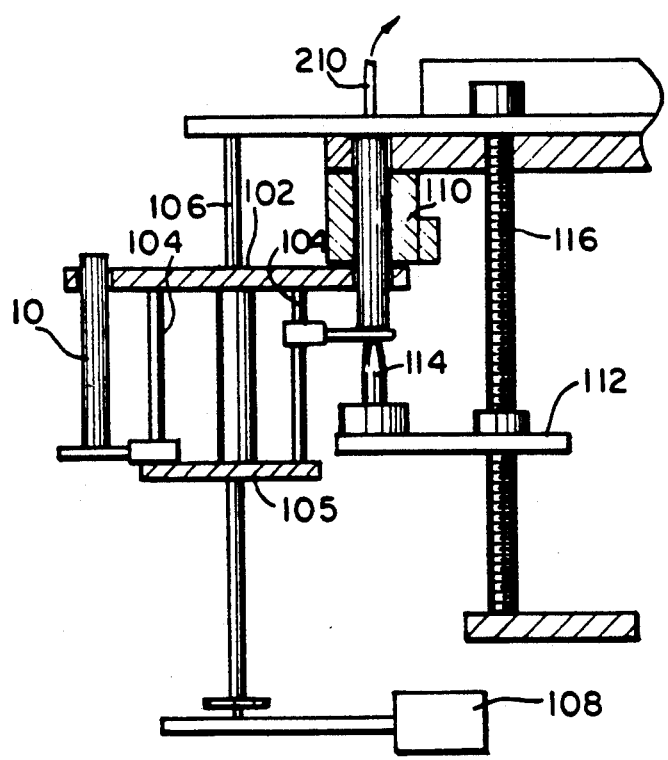

A carriage 112 and stripper 114, also shown in FIG. 1, are preferably provided to displace a sample container 10 from its position within the retaining means 102 and into communication with the sample input port 210. In a preferred embodiment, the carriage 112 is displaced by a pair of power screws 116. It will be understood, however, that there are numerous ways in which the required translation of the carriage 112 can be effected, for example, using a single power screw, a rack and pinion drive, belts and pulleys, or other types of systems. The means employed to move the carriage 112, and thus the stripper 114, must be capable of being precisely controlled and also capable of generating the force required to form a seal between the sample input port 210, the stripper 14 and the sample container 10, as described in greater detail below. Two limit switches 118 are preferably provided to govern the maximum and minimum travel of the carriage 112. The operation of the apparatus 100 illustrated in FIG. 1 and described above can be explained with reference to FIGS. 2A-2B, which provides a simplified diagrammatic view of portions of the apparatus 100 of the present invention. FIGS. 2A-2B illustrate the movement of a single sample container 10 using a stripper 14. In a most preferred embodiment, the sample container 10 is lifted fully into a thermal zone 110, as shown, for example, in FIG. 3. As seen in FIG. 2A, the stepper motor 108 rotates the retaining means 102 and aligns one of the sample containers 10 substantially between the stripper 114 and the sample input port 210, shown here along with the thermal zone 110 mentioned above. Referring now to FIG. 2B, it can be seen that upon rotation of the power screws 116, the carriage 112 and the stripper 114 are displaced and thereby move one of the sample containers 10 relative to its position within the retaining means 102, up into the thermal zone 110 and into communication with the sample input port 210. After processing, the sample container 10 is removed from communication with the input port 210 and lowered by reversing the rotation of the power screws 116. As explained in greater detail below, the stripper 114 is disengaged from the sample container 10 as it returns to its position within the retainer means 102. After the apparatus 100 has returned to the position illustrated in FIG. 2A, the retaining means 102 is moved to align another sample container in position for insertion, and the above-described process is repeated until all of the sample containers, or at least selected ones, have been processed. The present invention therefore presents a device that processes the plurality of sample containers 10 held in the retaining means in serial, and each sample within each sample container 10 has substantially the same sample history. It should be noted that the same result as that illustrated in FIG. 2A-2B can be achieved by other types of relative motion between the components described herein. For example, the retaining means could be moved downward while the stripper 114 holds a sample container stationary. A sample port connection and thermal zone could then be moved downward to engage the protruding sample. Numerous other variations of the relative motions of these components will present themselves as being useful.

Figure 3:
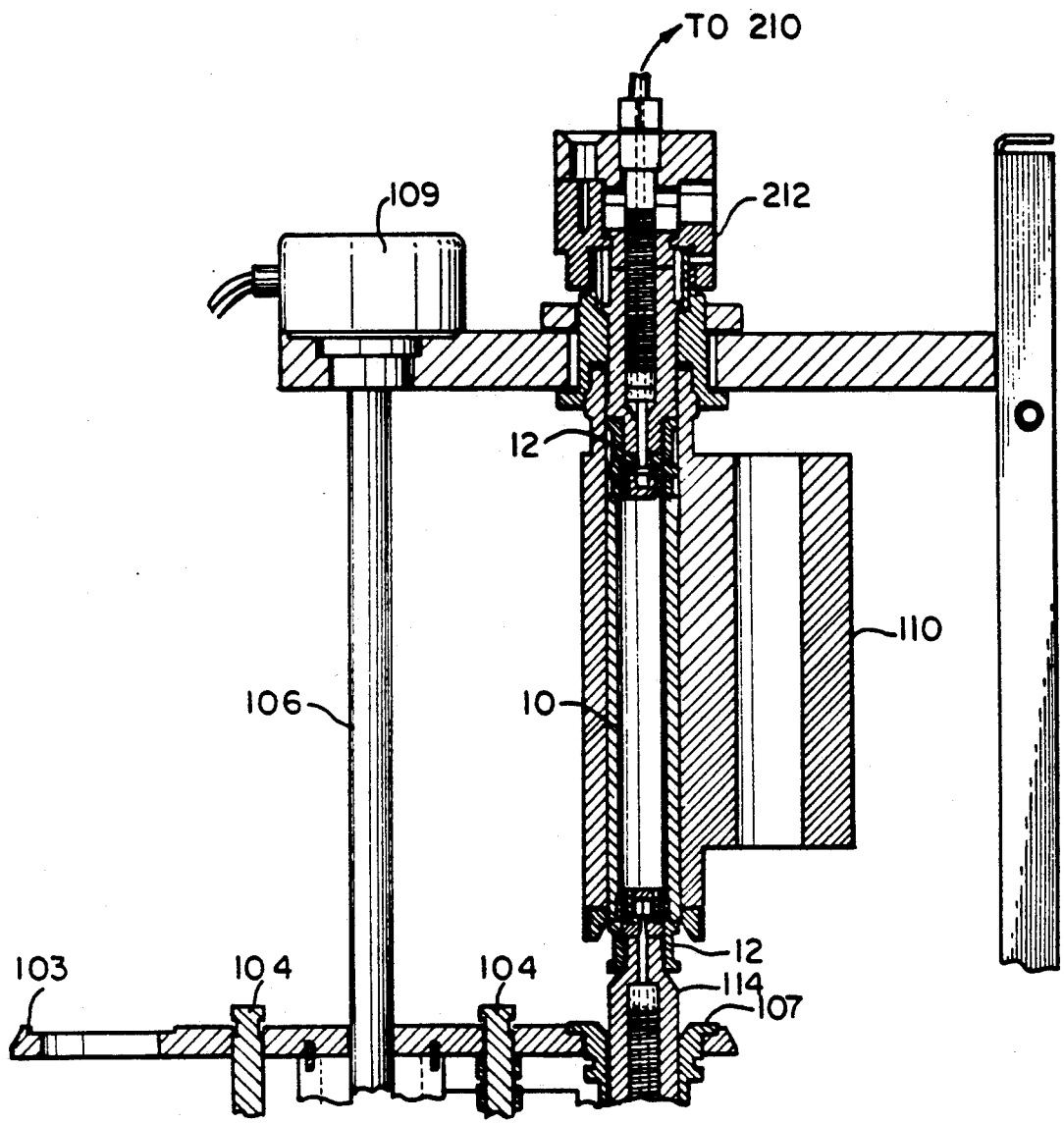
FIG. 3 is a cross-sectional elevation view, taken along lines 3—3 of FIG. 1 illustrating the details of the communication between a sample container and an instrument.

Referring now to FIG. 3, a partially broken away cross-sectional view of the apparatus depicted in FIG. 1 is illustrated. The components shown in FIG. 3 are in the position depicted in FIG. 2B, i.e., the movement of the carriage 112 (not shown in FIG. 3) has caused the stripper 114 to displace a sample container 10 from its sample retaining collar 107 within the top plate 103 of the retaining means 102 into the thermal zone 110 and also into communication with the sample input port 210. As will be understood by those of ordinary skill, the thermal zone 110 may comprise any of a number of devices, including conductive, convective or inductive jackets, including devices that use resistance heating coils or through which heated or cooled liquids flow, as well as solid state thermoelectric (Peltier) elements. Other forms of heating (or cooling) can be used, including microwave or other radiant types of heating. In the case of microwave heating, the components of the sample container 10 and the surrounding portions of the thermal zone should be constructed of non-metallic materials.

Details of the formation of the seal and communication between the sample container and the sample input port 210 are also visible in FIG. 3. As shown, the stripper 114 is most preferably adapted to cooperate with a recess formed in the sample container end cap 12. As explained above, this feature permits the stripper 114, through the force transferred by the power screws 116, to urge the end cap 12 into high pressure sealing engagement with the vessel being sealed. A similar engagement between an end cap 12 and a portion of the sample input port fitting 212 which is connected to and in communication with the sample input port 210 of the instrument 200 (not shown in FIG. 3). In those embodiments of the present invention where the end caps 12 are not constructed in accordance with the invention disclosed in U.S. patent application Ser. No. 825,450 filed Jan. 22, 1992, the details of the above-described engagement will differ, but the result achieved will be that the stripper 114 causes the sample container 10 to be placed in communication with the sample input port 210 so that the sample may be processed by the instrument 200.

Figure 4:
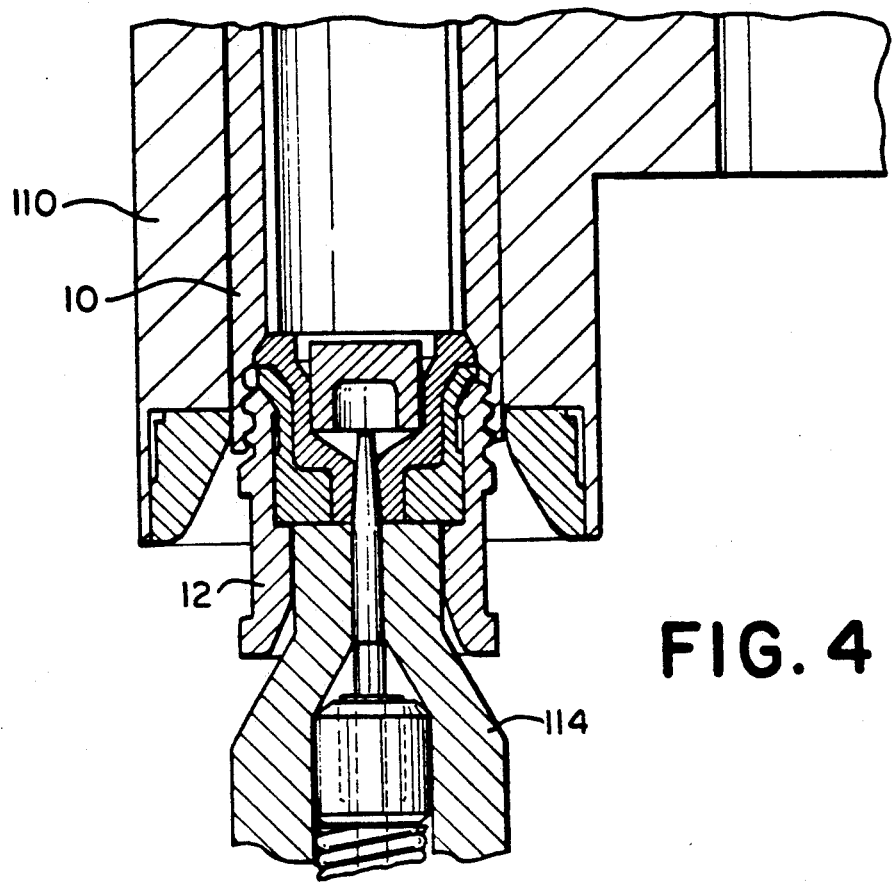
FIG. 4 is a partial cross-sectional view, of a portion of FIG. 3 depicting the engagement of a preferred embodiment of the apparatus of the present invention and a sample container.

The engagement of the stripper 114 and the end cap 12 is shown in greater detail in the enlarged, broken away view seen in FIG. 4, where it can be seen that the stripper 114 is preferably made to create an interference with a recess within the end cap 12. Preferably, the distal end of the stripper 114 is chamfered and split or otherwise constructed such that when encountering the interference of the end cap 12, there is a degree of compliance that permits a sliding frictional interference fit to be achieved. Due to this interference fit, the stripper will remain engaged with the end cap, and thus the sample container upon its withdrawal by the motion of the carriage 11 (not shown in FIG. 4). The withdrawal will be caused by a positive force, and thus reliance upon gravity is reduced. The positive force must be more than any resistive force created between either the coupling to the sample input port 210 or the thermal zone 110. The existence of this interference fit, however, requires that a means for disengaging the stripper 114 and the sample container 10 are preferably provided.

Referring again to FIG. 1, bottom arms 120 support the sample container 10 and also function to disengage the stripper 114 from the end cap 12 after the sample container 10 is withdrawn from communication with the sample port 210. As the carriage 112 moves the stripper 114 upwardly, the tapered end of the stripper 114 slides between the two sections of the bottom arms 120 and engages the recess in the end cap 12. The bottom arms 120 are slidably attached to the retaining means 102 and slide along the connecting rods 104 so that the upward movement of the sample container 10 is not inhibited. As the carriage 112 approaches its upper limit, the bottom arms 120 encounter a positive stop at the circular plate 103 and spread further apart as the stripper 114 continues to move upwardly. After processing, as the sample container 10 moves downwardly, the bottom arms 120 are biased to reengage the bottom of the sample container. The bottom arms then encounter and abut the lower plate 105 that forms part of the retaining means 102. Because the bottom arms 120 are disposed between the end cap 12 and the stripper 114, the stripper 114 is able to pull free of the end cap 12, since the bottom arms 120 create a resisting force.

Figure 5A:
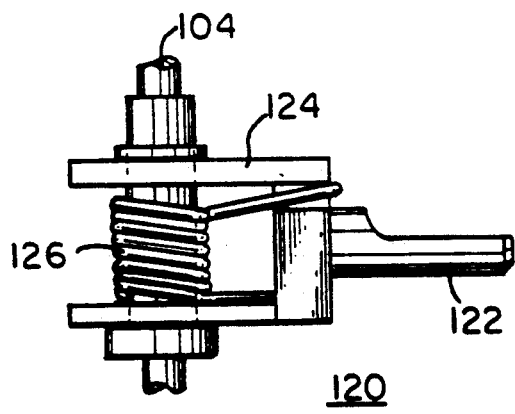
FIGS. 5A-5B are a side elevation and a plan view respectively of a portion of a preferred embodiment of the apparatus of the present invention for disengaging the sample container.
Figure 5B:
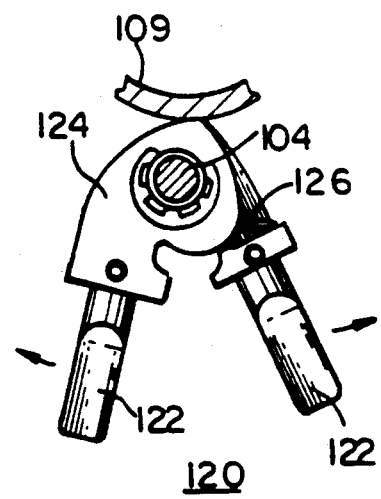

A preferred embodiment of the bottom arms 120 used in the present invention is illustrated in FIGS. 5A-5B. As shown, two arm sections 122 are affixed or attached to a spring biased hinge block 124. As seen in FIG. 5B, the arm sections 122 are hinged so that they can be moved away from one another to permit the stripper to pass through and engage the sample container 10, and then move further apart when the hinge block 124 encounters the top plate. The biasing force, preferably provided by a torsion spring 126, tends to force the arm sections 122 back together and provides the required engagement between the end cap 12 and the stripper 114 when the sample container is withdrawn from communication with the sample input port, as described above. The hinge block 124 is preferably shaped as illustrated in FIG. 5B so that when the lower arms 120 are assembled on to the connecting rods 104 they are prevented from rotating to a position that would prevent the distal end of the stripper from being able to be aligned between the arm sections 122. In other words, the shape of the hinge block 124 acts as a rotational limit stop against the center section 109 of the retaining means 102.

Another aspect of the present invention is the provision of the encoder 10 illustrated in FIG. 1 that permits initialization and control of the indexed rotation of the retaining means 102 that forms part of a preferred embodiment of the apparatus 100 made in accordance with the present invention. As mentioned above, since the rotation of the center axis 106 is less than a full revolution, a positional encoder can be used, and when initialized to a known position will function in the manner of an absolute encoder, thereby eliminating the need for a sensor to determine the rotational position of the retaining means 102. In order to accurately and repeatably accomplish such initialization, a base stop 130 and an axis stop 132 are provided. The base stop 130 is affixed to the apparatus in a predetermined location, while the axis stop 132 projects from and rotates along with the center axis 106. Most preferably, the base stop 130 is positioned so that when the axis stop 132 is lodged against it, as illustrated in FIG. 1, one of the locations for a sample container 10 is offset from alignment with the location from which it will be inserted into communication with the sample input port by a known displacement, e.g., 6.00°.

Thus, in order to initialize the apparatus disclosed herein, the stepper motor 108 or other drive mechanism rotates the center axis 106 at a first speed until the axis stop 132 encounters the base stop 130. Since there may be a slight rebound, the drive mechanism preferably "backs off" in the reverse direction and then attempts to slowly rotate the axis 106 at a second speed until a positive stop is achieved. Since this position is known, all the offsets for the location of each sample container are also known, and indexed rotation of the retaining means 102 can be accomplished. The initialization or homing routine is carried out each time the power is turned on in order to set the encoder count to zero. Those of ordinary skill will appreciate that there are other techniques by which accurate and reliable positioning of the retaining means 102 relative to the thermal zone 110 and the sample input port 210 may be accomplished. For example, active sensors or absolute encoders can be used, as well as other forms of hard stops or mechanical alignment schemes. The disclosed preferred embodiment, however, has been found to provide reliable alignment in a simple manner that is substantially unaffected by the removal of the retaining means 102, since the initialization procedure is automated.

Those of ordinary skill in the art will realize that there are a number of ways to effect the functions of the retaining means 102 and lower arms 120. The lower arms could be designed to be fixed or move in a stepwise fashion, or be actively controlled to "pinch" together at the required point in the travel of the sample container. The preferred embodiment shown in FIGS. 1 and 5A-5B has been found to be robust and reliable and does not require active controls or excessively complex mechanisms. The important feature of this aspect of the present invention is that the stripper 114 is dislodged from the end cap 12 in those embodiments of the present invention wherein a interference fit is created.

It will also be appreciated that the methods and apparatus disclosed herein are useful to permit the switching of separation columns such as employed in liquid chromatography, gas chromatography, supercritical fluid chromatography, size exclusion chromatography, solid phase extraction and well-known to those experienced in the art of separation. The invention then becomes a selector of columns —which can vary in packing identity such as from normal phase to reverse phase to size exclusion packings and which could also range from packed to capillary configurations. In such applications the pressures and flow rates will vary widely, from the lower pressures and flows encountered in liquid chromatography (LC) and/or biochemical processes to supercritical applications. These two aspects of the present invention can be combined to create an exceedingly flexible instrument, capable of manipulating both a queue of samples and having the ability to "switch" columns of different types or sizes. For example, in the field of extraction, solid phase extraction (SPE) certain embodiments will be useful that have both a rotating means for holding a plurality of sample containers and a second rotating means for holding a plurality of columns.

Although certain embodiments of the present invention have been disclosed and specifically described herein, these embodiments are for purposes of illustration and are not meant to limit the present invention. Upon review of this specification, certain improvements, modifications, adaptations and variations upon the methods and apparatus disclosed which do not depart from the spirit of the present invention will immediately become apparent. Accordingly, reference should be had to the appended claims in order to ascertain the true scope of the present invention.

What is claimed is:

1. A method of handling a plurality of sample containers to be placed into communication with an instrument comprising a sample input port, wherein the plurality of sample containers are disposed in lower arms of a retaining means, and wherein the sample container is guided by a stripper assembly to place the sample container into fluid communication with the input port, the method comprising the steps of:

indexing the retaining means to substantially align one of the sample containers with the sample input port;

creating a mechanical connection between the sample container and a stripper assembly by moving the stripper assembly through the lower arm to engage an end cap of the sample container;

moving the sample container into fluid communication with the input port by displacing the sample container from the retaining means using the stripper assembly and the lower arm;

urging the sample container against the input port to create an interference fit connection between the end cap of the sample container and the stripper assembly by moving the stripper assembly and the lower arm together until the lower arm encounters a positive stop that prevents further motion of the lower arm, thereby allowing further motion of the stripper assembly for urging the sample container against the input port;

operating the instrument to interact with a sample contained in the sample container; and disengaging the mechanical connection between the sample container and the stripper assembly by moving the stripper assembly and the lower arm together in an opposite direction until the lower arm encounters and abuts a plate that prevents further motion of the lower arm, thereby further motion of the stripper assembly causes the step of disengaging the mechanical connection between the sample container and the stripper assembly.

2. The method of claim 1, wherein the retaining means comprises a circular rack disposed about a center axis, wherein the step of indexing the retaining means comprises rotating the circular rack about the center axis for a predetermined portion of a revolution.

3. The method of claim 1, wherein the step of operating the instrument to interact with the sample comprises moving the sample container and the sample contained therein into a thermal zone and performing the operating step while the sample container is disposed within the thermal zone.

4. The method of claim 1 further comprising a preliminary step of initializing a position of the retaining means relative to the sample input port.

* * * * *